United States Patent [19]

Noguchi et al.

[11] Patent Number: 5,257,092
[45] Date of Patent: Oct. 26, 1993

[54] APPARATUS FOR MEASURING POLARIZATION AND BIREFRINGENCE

[75] Inventors: Masato Noguchi; Tsuyoshi Ishikawa, both of Tokyo, Japan

[73] Assignee: Asahi Kogaku Kogyo Kabushiki Kaisha, Tokyo, Japan

[21] Appl. No.: 721,694

[22] Filed: Jun. 26, 1991

[30] Foreign Application Priority Data

| Jun. 27, 1990 | [JP] | Japan | 2-170998 |
| Jun. 27, 1990 | [JP] | Japan | 2-170999 |
| Jun. 27, 1990 | [JP] | Japan | 2-171000 |

[51] Int. Cl.$^5$ ............................................. G01N 21/23
[52] U.S. Cl. ........................................ 356/367; 356/124
[58] Field of Search ............... 356/124, 364, 365, 366, 356/367, 369

[56] References Cited

U.S. PATENT DOCUMENTS

| 3,810,698 | 5/1974 | Alaska | 356/124 |
| 3,815,997 | 6/1974 | Alaska | 356/336 |
| 3,902,805 | 9/1975 | Redner | 356/367 |
| 3,992,571 | 11/1976 | Garleck et al. | 356/365 |
| 4,035,082 | 7/1977 | Kirschen | 356/124 |
| 4,310,242 | 1/1982 | Genco et al. | 356/365 |
| 4,516,855 | 5/1985 | Korth | 356/367 |

FOREIGN PATENT DOCUMENTS

63-269045 11/1988 Japan .

OTHER PUBLICATIONS

Walraven, R. "Polarization imagery" *Optical Engineering* vol. 20, No. 1 (Jan./Feb. 1981) pp. 14-18.

English abstract of Japanese Patent Publication No. SHO 63-269045. Nov. 7, 1988.
English and Japanese versions of "New Development of Interference Measurement-Fringe Scanning Interferometry" by Toyohiko Tanidagai Nov. 1983.
"Dynamic Imaging Microellipsometry: Theory, System Design, and Feasibility Demonstration", Cohn et al., Applied Optics, pp. 4664-4671, vol. 27, No. 22, Nov. 15, 1988.

*Primary Examiner*—Richard A. Rosenberger
*Attorney, Agent, or Firm*—Sandler Greenblum & Bernstein

[57] ABSTRACT

A polarization and birefringence measuring device has an optical source which causes a wide polarized light beam to impinge on a specimen. A photodetecting sensor having picture elements in two dimensions detects a light beam containing information about the specimen. A analyzer is situated in front of the photodetecting sensor and rotated to vary the amount of light which is transmitted. A frame memory memorizes the intensity of each picture element in the photodetecting sensor, and a computer determines the polarization state of parts of the specimen coresponding to the intensity of each picture element sampled. The computer samples the output of the photodetecting sensor when the rotation angle of the analyzer has reached a specified value, and this is memorized by the frame memory. As it may be assumed that the intensity variation of the light beam produced by the rotation of the analyzer is sinusoidal, its polarization state for each picture element can be found by performing no less than three measurements.

16 Claims, 6 Drawing Sheets

APPARATUS FOR MEASURING POLARIZATION AND BIREFRINGENCE

BACKGROUND OF THE INVENTION

1. Field of the Invention

This invention concerns an apparatus for measuring the polarization state of an incident light beam of a given width, the polarization properties of lenses, and the birefringence of optical elements.

2. Description of the Prior Art

In the prior art, devices that can measure polarization have been used to measure the polarization properties of elements, such as optical parallel plates. In conventional devices, a polarizer and an analyzer are disposed between an optical source that emits a light beam of a diameter of approximately 1 mm, and a photodetector, the element to be measured being interposed between these polarizing plates, and the amount of light transmitted being detected while the analyzer is rotated.

It is then possible to calculate at least the inclination of the polarization ellipse from the amount of light detected and the rotation angle of the analyzer.

These conventional devices, however, perform measurements on a narrow light beam. To obtain information in two dimensions, a mechanism was necessary to scan the specimen, which necessarily made the device more complex. And the measurement itself took a considerable time to perform.

Further, conventional devices were able to measure the polarization properties only of reflecting surfaces and flat plates, and could not be used to measure the polarization of lenses.

Conventional devices to measure the property of birefringence, on the other hand, are disclosed in Japanese Patent Early Laid-open Publication No. Sho 63-269045.

In the devices described in this Publication, the specimen is placed between a polarizer and an analyzer arranged in an orthogonal Nicol fashion, and the transmitted beam is received by a video camera while the orthogonal Nicol is rotated. In this measurement, the maximum light intensity and the rotation angle which gives this maximum intensity are found, and the birefringence of the specimen is calculated as a function of the rotation angle of the Nicol.

To measure birefringence with the above device, however, the light intensity must be measured with respect to a rotation angle of the Nicol at a large number of points. The measurement therefore requires a considerable amount of time, and the large amount of data obtained also requires a considerable amount of time to process.

SUMMARY OF THE INVENTION

The main objective of this invention is therefore to provide a device which can measure the polarization state of a light beam of a given width, the polarization properties of a specimen or the birefringence of a specimen in a short time with a high precision without having to scan with a light beam.

A further objective of the invention is to provide a device which can measure the polarization properties or the birefringence of a lens.

DETAILED DESCRIPTION OF THE EMBODIMENTS

The embodiments of the present invention will now be described hereinafter with reference to the drawings. The present disclosure relates to subject matter contained in Japanese Patent Applications Nos. HEI2-170998, HEI2-170999 and HEI2-171000 (all filed on Jun. 27, 1989) which are expressly incorporated herein by reference in their entireties.

EMBODIMENT 1

Figure 1:
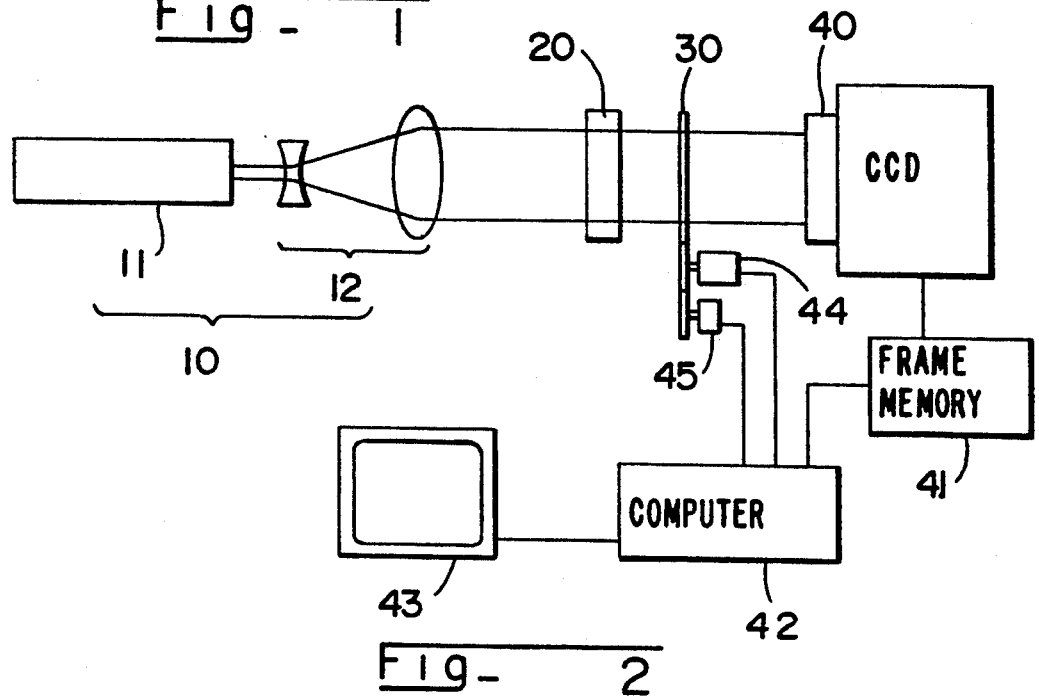
FIG. 1 is a schematic drawing of a first embodiment of a polarization and birefringence measuring device of the present invention.

FIG. 1 is a schematic drawing of a first embodiment of a polarization and birefringence measuring device of this invention.

This device comprises an optical source unit 10 which causes a linearly polarized light beam of a given width to impinge on an optical parallel plate 20, an analyzer 30 that is arranged such that it is free to rotate in the path of the light beam transmitted by the plate 20, a two dimensional image sensor 40, such as a CCD sensor that detects the light beam transmitted by the analyzer 30, a frame memory 41 which performs an A/D conversion on the output of the image sensor 40 and memorizes it, a computer 42 which analyzes the data in the frame memory 41 at no less than three different angular settings of the analyzer 30, and a display terminal 43 which displays the results of the analysis.

The optical source unit 10 comprises a light source 11, such as a laser, which emits linearly polarized light, or a device which emits a light beam with random polarization and a polarizer, and a beam expander 12 which increases the diameter of the light beam emitted by the optical source 11.

The analyzer 30 is automatically rotated by a motor 44, and the rotation angle is inputted from an angle sensor 45 to the computer 42.

When polarization properties are measured by the above apparatus, the plate 20 is arranged between the optical source unit 10 and the analyzer 30, the optical source is switched on to pass a light beam through the system, and the analyzer 30 is rotated.

The computer 42 samples the output of the image sensor 40 when the rotation angle of the analyzer 30 has reached a specified value, as determined by the angle sensor 45, and this is then memorized by the frame memory 41. As it may be assumed that a intensity variation of the light beam produced by the rotation of the analyzer 30 is sinusoidal, its polarization state for each picture element can be found by performing no less than three measurements.

Figure 2:
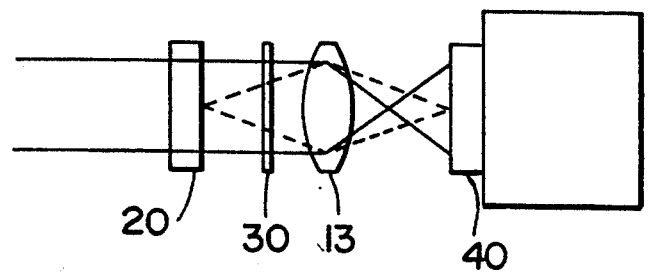
FIG. 2 is a schematic drawing of one modification of the first embodiment.

FIG. 2 shows an example where an imaging lens 13 is placed between the analyzer 30 and image sensor 40 in the above arrangement, and an image produced by the plate 20 is formed on the image sensor 40.

Figure 3:
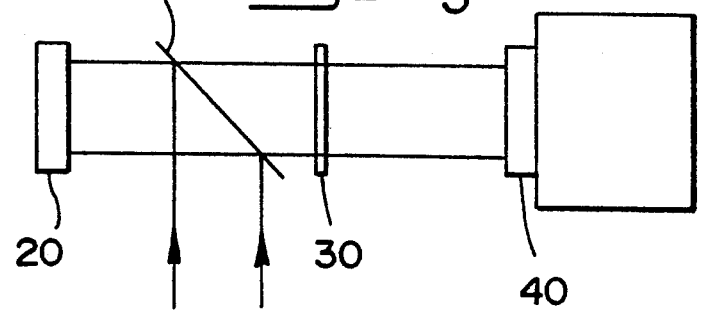
FIG. 3 is a schematic drawing of another modification of the first embodiment.

In the device shown in FIG. 3, a half mirror HM is placed between a plate 20 which has a reflecting surface and the analyzer 30, and the polarization state of a light beam incident from the bottom of the figure and reflected by the plate 20 is measured.

We shall now describe the principle whereby this device measures a polarization. It should first be understood that this device measures the polarization state in different parts of a light beam of a given width, (i.e., the degree of elliptical polarization) and it does not measure only the change of polarization properties of a specimen.

Figure 4:
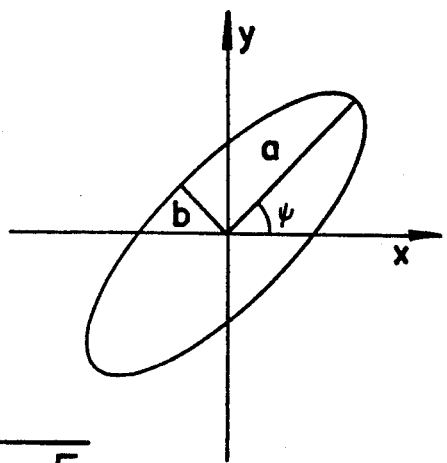
FIG. 4 is a graph of a polarization ellipse.

To express an elliptical polarization, as shown in FIG. 4, one needs to know the long diameter a, short diameter b and inclination $\phi$ of the ellipse formed by the tip of the electrical field vector in a plane opposite to the direction of progression of the wavefront. When either a or b is zero, the polarization is linear, and when a=b, it is circular.

An intensity I of this elliptically polarized light detected via the analyzer may be found from equation (1), where $\theta$ is the rotation angle of the analyzer:

$$I = \alpha + \beta \cdot \cos 2(\theta - \phi) \quad (1)$$

where:
$\alpha = (a^2 + b^2)/2$
$\beta = (a^2 - b^2)/2$.

Figure 5:
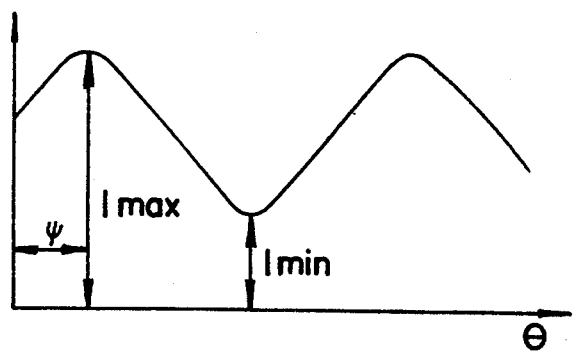
FIGS. 5 and 6 are graphs showing the variation in the amount of light received by a photodetecting means when an analyzer is rotated.

Ideally, as shown in FIG. 5, the intensity I will vary as a sine wave depending on the rotation angle $\theta$ of the analyzer 30. The maximum and minimum intensities Imax and Imin are given by the following relations, respectively:
Imax = $a^2$
Imin = $b^2$.

Equation (1) has three unknown parameters which express polarization properties $\alpha$, i.e. $\beta$, and $\phi$. The values of these three unknowns can therefore be determined by measuring the output intensity I when the analyzer 30 is rotated to three different angular settings. Here, in order to simplify the calculation, we take four measurements at 45° intervals. The following relations exist between the above three parameters and the intensities I0, I45, I90 and I135 obtained in the four measurements:

$$I0 = \alpha + \beta \cdot \cos(-2\phi) = \alpha + \beta \cdot \cos 2\phi$$

$$I45 = \alpha + \beta \cdot \cos(90° - 2\phi) = \alpha + \beta \cdot \sin 2\phi$$

$$I90 = \alpha + \beta \cdot \cos(180° - 2\phi) = \alpha - \beta \cdot \cos 2\phi$$

$$I135 = \alpha + \beta \cdot \cos(270° - 2\phi) = \alpha - \beta \cdot \sin 2\phi.$$

These intensities are measured as independent data for each picture element of the image sensor 40, and are memorized by the frame memory 41 as image information for each of the four angles at which the measurement is made. Each time four measurements have been completed, the computer 42 uses the four intensity data to compute the parameters expressing polarization properties for each picture element according to the following relations:

$$\alpha = \frac{I0 + I45 + I90 + I135}{4}$$

$$\beta = \sqrt{\frac{(I0 - I90)^2 + (I45 - I135)^2}{4}}$$

$$\phi = \frac{1}{2} \cdot \tan^{-1}\left(\frac{I45 - I135}{I0 - I90}\right)$$

When the analysis is complete, the inclination $\phi$ of ellipse, for example, is converted to a light or dark shade on the display terminal 43, or converted to a dot size and printed out. However, instead of displaying the parameters for individual picture elements, the differences between parameters for adjacent elements are displayed so as to give an overall visual representation of the polarization properties of the specimen.

The resolution which is possible in this measurement depends on the number of picture elements in the image sensor 40, but with modern high density sensors, much higher precision is obtainable than by conventional measurement in 1 mm diameter units.

If, in the above measurement, there is noise due to soiling of the specimen surface, an accurate determination is still possible for $\phi$, but not for $\alpha$ and $\beta$.

Figure 6:
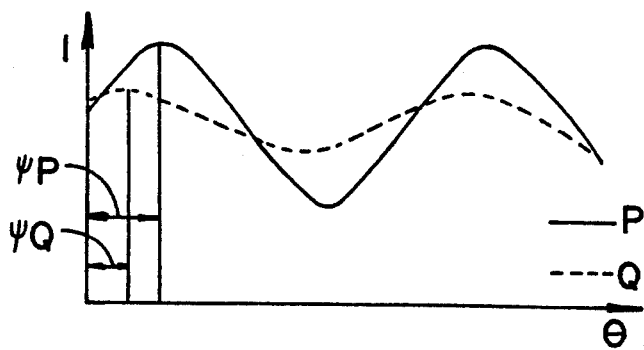

If the device is set on the specimen at a point P where there is no noise and a point Q where there is noise, for example, the sine wave shown by P in FIG. 6 is outputted from picture elements in the image sensor that receive the light beam from point P, and the sine wave shown by Q in FIG. 6 from picture elements corresponding to point Q. These sine waves have different amplitudes, depending on whether noise is present or absent, but their wavelength is the same, and the phase difference between them, (i.e., the difference between inclination $\phi P$ and $\phi Q$) can be precisely found.

When the effect of noise can be ignored, (i.e., when the values of $\alpha$ and $\beta$ can be found with high reliability) information concerning the birefringence of the specimen may also be obtained by determining the phase difference between an ordinary ray and an extraordinary ray, based on the light emerging from the specimen when linearly polarized light is incident on it.

Further, in the above embodiment, we have described only the measurement of the light emerging from the specimen. This invention is, however, not limited only to this embodiment, and in a more general sense, it can, for example, be used effectively to measure the polarization of a light beam of given width, i.e., the polarization of a a light beam irrespective of the system from which it is generated.

Using the device for measuring polarization and birefringence of this embodiment, the polarization state of a light beam of a given width or the birefringence of an optical element can be determined in one step without the need to scan with the light beam. The mechanical construction of the device can therefore be simplified, and the time required for processing data is shorter.

EMBODIMENT 2

Figure 7:
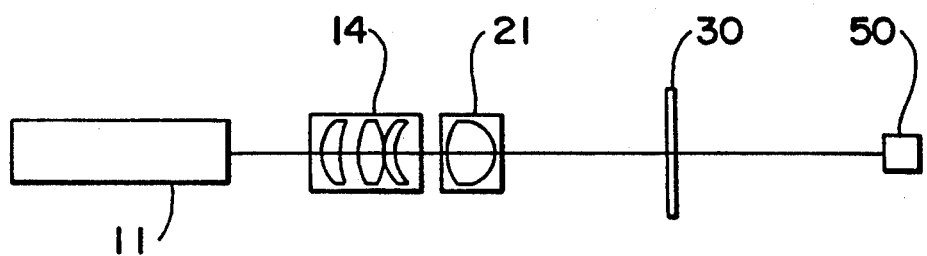
FIG. 7 is a schematic drawing of a second embodiment of a polarization measuring device of the present invention.

FIG. 7 shows a second embodiment of the polarization measuring device of this invention.

This device comprises a He-Ne laser 11 which emits linearly polarized light, an analyzer 30 that is free to rotate in the optical path of the laser, and a photodetector 50 that detects the amount of light in the beam that has passed through the analyzer 30.

To carry out a measurement, an adjusting lens 14 is arranged depending on the power of a test lens 21, such that the laser light emerging from the lens 21 is parallel when it impinges on the analyzer 30. That is, the adjusting lens 14 and the test lens 21 comprises an afocal system. The optical source unit 10 comprises the adjusting lens 14 and the laser 11. The test lens 21 is a convex lens in this example, but the adjusting lens 14 can be arranged to make the light beam parallel and the same measurement can be made even if test lens 21 is concave.

Ideally, when the analyzer 30 is rotated, the output of the photodetector 50 will vary sinusoidally. By comparing the polarization state of the light incident on the test lens 21 with the change in the polarization of the emergent light, the polarization properties of the test lens 21 can be measured at the point where the light beam passes through it, and by scanning it with the light beam, two dimensional information about the test lens 21 can be obtained.

As the analyzer 30 has an angular dependence, the amount of light reaching the photodetector 50 may also vary due to factors other than polarization properties if the incident light beam is not parallel. The device is therefore arranged to make the light emerging from the test lens 21 parallel.

Further, if the test lens 21 is small, the space between the test lens 21 and the imaging lens 13 would be shorter and there would be no space for the analyzer if there were no adjusting lens 14. Sufficient space must therefore be allowed for the adjusting lens.

To measure the whole surface of the test lens 21, the numerical aperture of the adjusting lens 14 must be greater than that of the test lens 21.

If the power of the test lens 21 to be measured is uniform, the power of the adjusting lens 14 may be chosen accordingly, but if test lenses of different power are to be measured, the adjusting lens 14 may consist of a zoom lens or variable focus lens of which the focal length can be varied.

The polarization measurement principle is identical to that of the first embodiment above.

The polarization properties measured by the device of the second embodiment include the effect of not only the test lens 21 but also of the adjusting lens 14. If, however, the polarization properties of the lens 14 are found beforehand, their effect may be subtracted in order to determine the polarization properties of the lens 21. The adjusting lens 14 should preferably be a glass lens with no birefringence so that there are less discontinuities in its polarization properties. However, a plastic lens may also be used without any problem, provided its polarization properties are first measured by the following method.

To measure the polarization properties of the adjusting lens 14, a pair of identical adjusting lenses 14, 14 are arranged back-to-front between the laser 10 and analyzer 30, such that the light emitted to the analyzer 30 is parallel. The polarization properties of the adjusting lens 14 can then be measured using the same method as above with twice the sensitivity.

Figure 8:
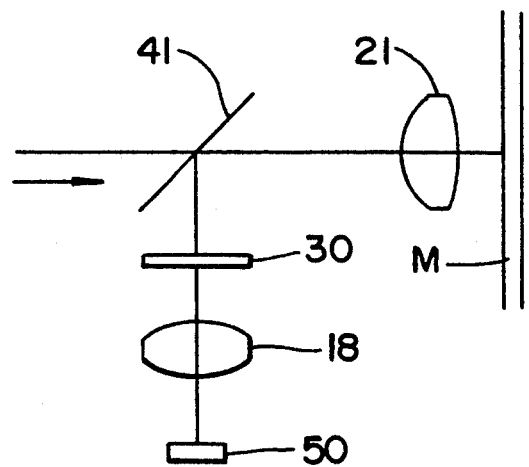
FIG. 8 is a schematic drawing of one modification of the second embodiment.

To measure the polarization properties of an optical system such as an magneto-optic disk device, as shown in FIG. 8, the test lens 21 is arranged as an objective lens in front of a reflecting plate M corresponding to a disk in the same way as it would be used in practice, and a parallel light beam is made to impinge on it. The light beam reflected from the plate M passes through the test lens 21 again, is reflected by a half mirror 41, and is converged by a converging lens 18 via the analyzer 30, which is free to rotate, onto the photodetector 50.

The measurement principle is identical to that of the second embodiment. By rotating the analyzer 30 and measuring the variation in the amount of light detected, the polarization properties of an objective lens as it would be used in an actual set-up can be measured. In this case, as the light beam passes through the objective lens and then returns through it, the emergent light is a parallel beam, even if an adjusting lens is not used on the incident side.

EMBODIMENT 3

Figure 9:
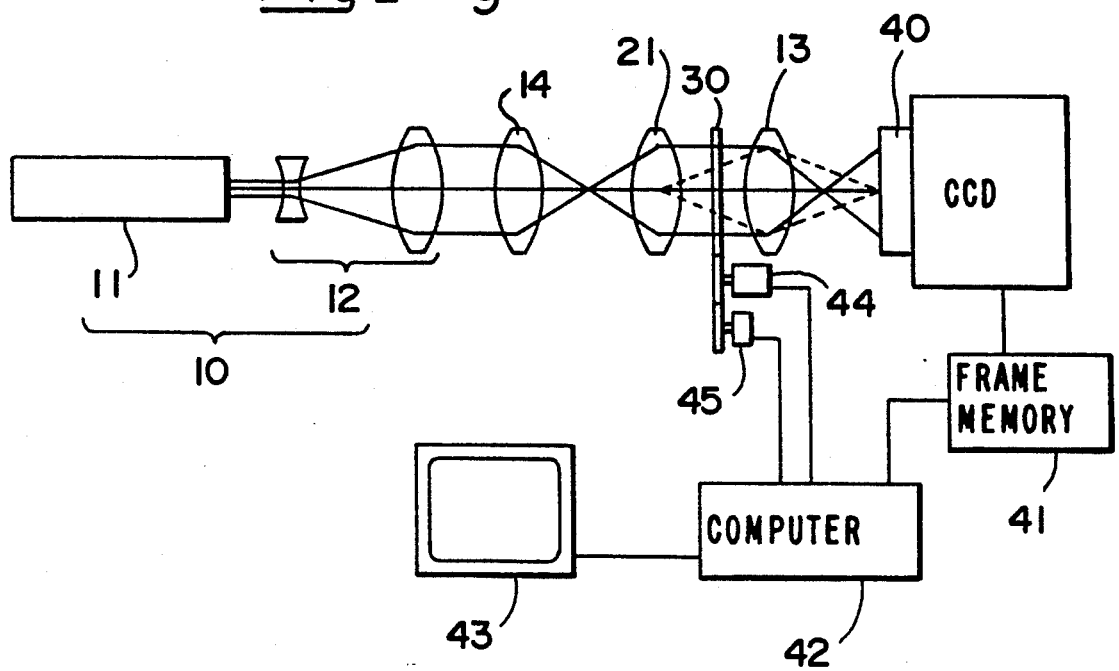
FIG. 9 is a schematic drawing of a third embodiment of a polarization and birefringence measuring device of the present invention.

FIG. 9 shows a third embodiment of the polarization measuring device of this invention.

This device comprises an optical source unit 10 which emits a linearly polarized light beam of a given width, an adjusting lens 14 which converges the beam such that it is parallel after passing through a test lens 21, an analyzer 30 which is free to rotate in the optical path of the beam that has passed through the lens 21, and an imaging lens 13 which forms an image of the light beam emerging from the analyzer 30. The remainder of the construction is identical to that of the device in FIG. 1.

To measure the polarization properties of a speciment with this device, the test lens 21 is arranged between the adjusting lens 14 and analyzer 30, the optical source is switched on to pass a light beam through the system, and the analyzer 30 is rotated. The measurement principle is identical to that of the device in FIG. 1.

Using this device, the scatter in the polarization properties of a lens can be given an overall visual representation.

Figure 10:
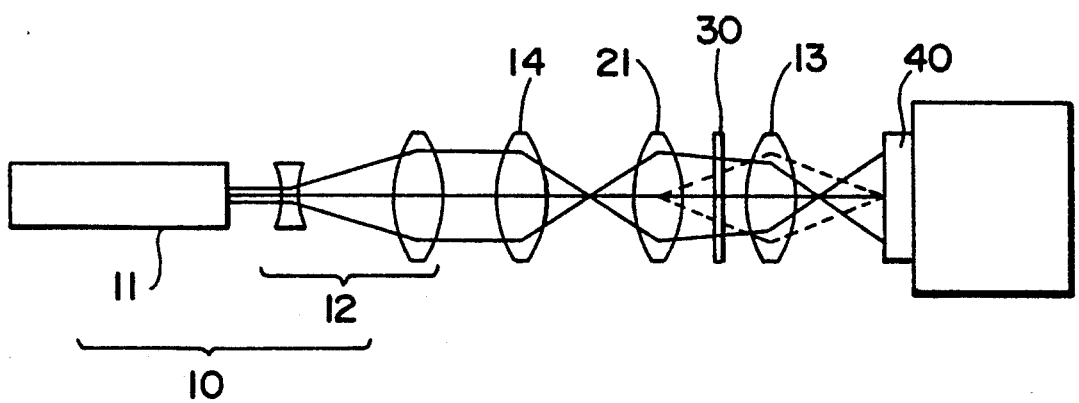
FIG. 10 is a schematic drawing of one modification of the third embodiment.

FIG. 10 shows a modification of Embodiment 3. In this example, the test lens 21 is arranged such that it converges the emergent light beam. This arrangement is suitable for measuring the polarization properties of the lens 21 when it is to be used as a converging lens. Since the measurement is made with the lens 21 in an actual use situation, its behavior in actual use can be reproduced more faithfully. The remainder of the construction is identical to that of FIG. 9.

EMBODIMENT 4

Figure 11:
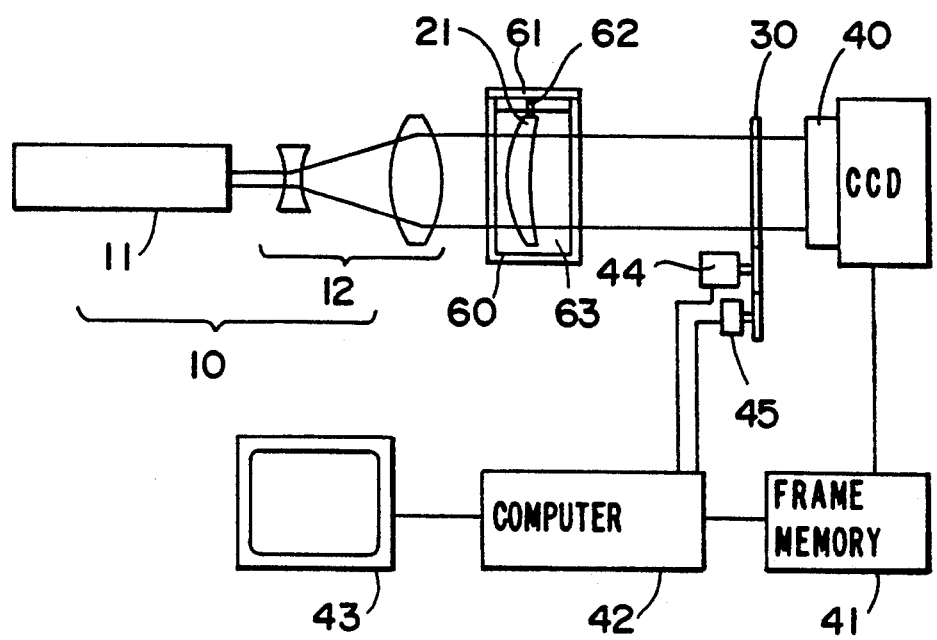
FIG. 11 is a schematic drawing of a fourth embodiment of a polarization and birefringence measuring device of the present invention.

FIG. 11 shows a fourth embodiment of the polarization and birefringence measuring device of this invention.

In this example, the test lens 21 is immersed in a matching fluid in a tank 60. A fixing piece 62 is provided in a lid 61 of the tank 60. The test lens 21 is secured by means of the fixing piece 62, and the tank is filled with a matching fluid 63. The matching fluid 63 has the same effective refractive index as the test lens 21 and no optical rotatory power.

To measure a plastic lens made of polymethyl methacrylate (acrylate), the matching fluid 63 may, for example, consist of a mixture of a dimethyl silicone oil and a phenylmethyl silicone oil.

The matching fluid 63 may also consist of immersion fluids for mineral research, such as, cedar oil or clove oil, or other silicone oils.

The factors which cause the polarization state of an optical element to vary are its surface shape and the birefringence of the material of which it is made. By immersing the test lens 21 in a matching fluid 63, the effect of the surface shape of the lens can be eliminated, and the birefringence of the material can be measured alone.

Using this method, it is therefore possible to measure the birefringence of elements with a complex shape, such as, for example, aspherical lenses, or elements which do not form an image.

The remainder of the construction and the measurement principle are identical to those of the first embodiment.

Figure 12:
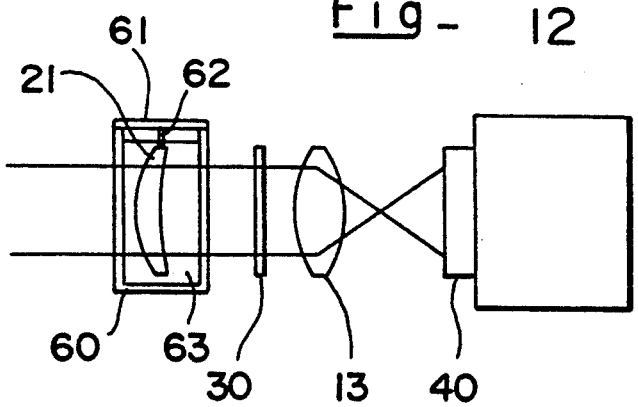
FIG. 12 is a schematic drawing of one modification of the fourth embodiment.

FIG. 12 shows an arrangement where an imaging lens 13 is interposed between the analyzer 30 and image sensor 40 of the device in the fourth embodiment, and an image of the test lens 21 is formed on the image sensor 40.

EMBODIMENT 5

Figure 13:
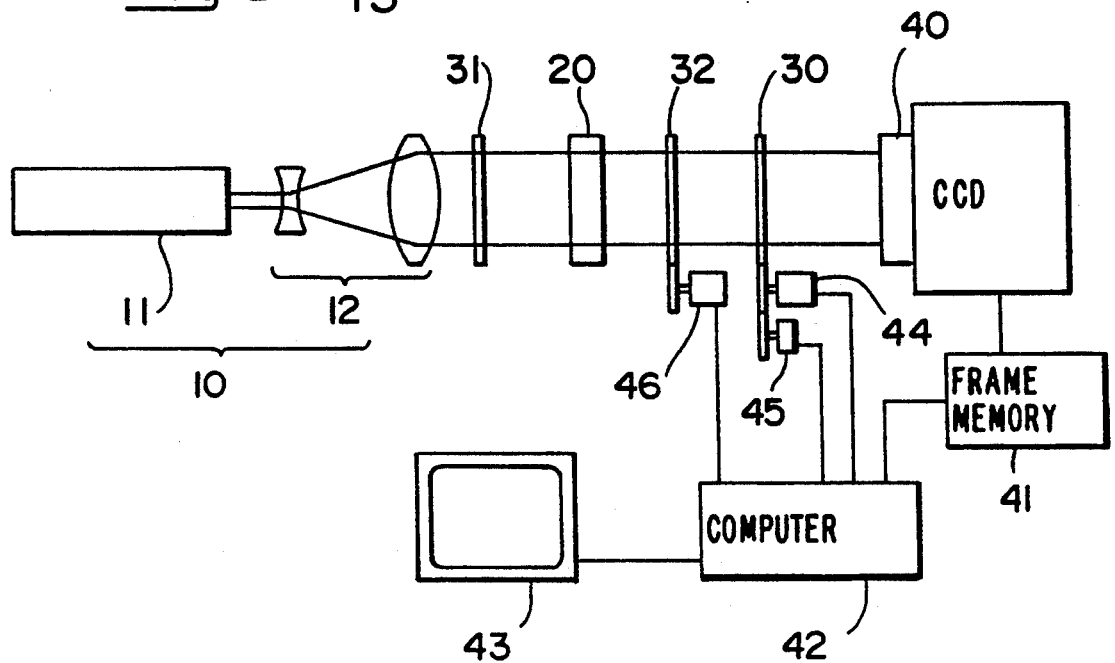
FIG. 13 is a schematic drawing of a fifth embodiment of a birefringence measuring device of the present invention.

FIG. 13 shows a fifth embodiment of the polarization and birefringence measuring device of this invention.

If there is dirt or other foreign matter on the specimen being measured, noise is generated so that it is difficult to precisely measure birefringence using the device of the first embodiment. Further, in the device of the first embodiment, linearly polarized light is made to impinge on the specimen. If a plastic specimen is measured and the polarization of the incident light is coincide with the natural polarization of the specimen, the light is transmitted without any change of polarization state and birefringence cannot be measured.

The fifth embodiment provides a device which permits a precise measurement of birefringence, even when there is dirt on the surface of the specimen, and which permits measurement of birefringence independently of the natural polarization of the specimen.

This device comprises an optical source unit 10 which emits a linearly polarized light beam of a given width, a first ¼ wave plate 31 which converts the beam emitted by the optical source to circularly polarized light, a second ¼ wave plate 32 acting as a phase shifter which converts the light beam transmitted by the specimen, such as an optical parallel plate 20, to near-linear elliptically polarized light, an analyzer 30 that is free to rotate in the optical path, and a two dimensional image sensor 40, such as a CCD sensor, which detects the light beam transmitted by the analyzer 30. The output of the image sensor 40 is subjected to an A/D conversion, memorized by a frame memory 41, analyzed by a computer 42, and displayed by a display terminal 43 as birefringence information.

The optical source unit 10 comprises a light source 11, such as a laser, which emits linearly polarized light or a device which emits a light beam with random polarization and a polarizer, and a beam expander 12 which increases the diameter of the light beam emitted by the optical source 11.

The second ¼ wave plate 32 is free to rotate about the optic axis, such that, upon instructions from the computer 42, it can be set at no less than two different angles by means of a motor 46.

The analyzer 30 is rotated automatically by a motor 44, and its rotation angle is inputted from an angle sensor 45 to the computer 42.

To measure the polarization properties of a specimen with the above device, the plate 20 is interposed between the first and second ¼ wave plates 31 and 32. Circularly polarized light is made to impinge on the plate 20, and the emergent light beam is detected via the second ¼ wave plate 40 and analyzer 30.

When circularly polarized light is made to impinge on a specimen with birefringence, the wavefront progresses at different speeds along two orthogonal axes due to the difference of refractive index along the slow phase axis and the fast phase axis. The light therefore emerges with an elliptical polarization. This elliptically polarized light is again passed through a phase shifter, such as a ¼ wave plate, to convert it to near-linear elliptically polarized light, and then passed through the analyzer.

By rotating the analyzer, the amount of light detected varies sinusoidally, and the polarization state can be measured by sampling this variation at several points. If circularly polarized light is made to impinge on the specimen, unlike the case of linear polarization, the specimen does not have a dead direction. The polarization properties may thus be measured in any direction.

The closer the light measured is to linear polarized light, the greater is the variation in the amount of light reaching the image sensor 40, and the better is the precision of the measurement. The phase shifter may conveniently be a ¼ wave plate to produce the near-linear elliptical polarization required.

The polarization of the light beam may be measured by the same method as that of the first embodiment.

It has already been described that when polarization properties are measured based only on intensities, dirt on the specimen is interpreted as an intensity variation. The signal is therefore accompanied by noise, and a precise measurement of polarization properties cannot be made.

To take account of the effect of noise, we may write:

$$I = \alpha + ns + (\beta + nm) \cdot \cos 2(\theta - \phi)$$

where the light intensity detected is I, summed noise is ns, and multiplied noise is nm. When noise is present, the parameters $\alpha$ and $\beta$ cannot be determined precisely, although the inclination of the polarization ellipse with respect to the main axis $\phi$ is not affected by noise, and can be accurately found.

Summed noise may refer in the optical sense to noise produced when light other than that used for measurement impinges on the image sensor 40, while in the electrical sense, it may refer to an error in an offset adjustment of, for example a television signal. Multiplied noise may refer in the optical sense to noise produced by non-uniformity of illumination, and in the electrical sense, to scatter in the sensitivity of picture elements of a CCD.

To measure birefringence, it is necessary to determine an axial direction of the birefringence and the amount of retardation. In the method of this invention, the above parameter $\phi$ is analyzed no less than twice by varying the angle setting of the phase shifter.

In the first step, a neutral axis of the second $\frac{1}{4}$ wave plate 32 is set at 45° to a neutral axis of the first $\frac{1}{4}$ wave plate 31. The computer 42 samples the output of the image sensor 40 when the angle sensor 45 indicates that the rotation angle of the analyzer 30 has reached a specified value, and inputs it to the frame memory 41.

In the second step, the neutral axis of the second $\frac{1}{4}$ wave plate 32 is set at 0° to the neutral axis of the first $\frac{1}{4}$ wave plate 31. The output of the image sensor 40 is then sampled at no less than three different rotation angles of the analyzer, as in the first step, and the polarization state of the light beam for each picture element is measured.

Based on the intensity information in picture element units memorized by the frame memory 41, the computer 42 calculates a value $\xi$ corresponding to $\phi$ in the first step, and a value $\eta$ corresponding to $\phi$ in the second step.

If we assume that a retardation is less than $\pi/2$, retardation $\delta$ and axial direction $\theta$ may be determined according to the following principle if we are measuring only $\phi$ for light which has near-linear polarization.

If left-hand circularly polarized light is made to impinge on a specimen with a retardation $\delta$ and an axial direction $\theta$, the output light when the light emerging from the specimen is passed through a $\frac{1}{4}$ wave plate set at 45°, X45, may be represented by the following vector:

$$X45 = \begin{bmatrix} \cos\frac{\delta}{2} \\ \sin\frac{\delta}{2} e^{i2\theta} \end{bmatrix}$$

The direction of the long axis of the polarization ellipse for this output light X45 is given by equation (2):

$$\tan 2\xi = \tan \delta \cos 2\theta \quad (2)$$

Further, if the angle of the $\frac{1}{4}$ wave plate is set to 0°, the output light X0 is given by the following vector:

$$X0 = \begin{bmatrix} \cos\frac{\delta}{2} + \sin\frac{\delta}{2} e^{i(\pi/2-2\theta)} \\ -\cos\frac{\delta}{2} + \sin\frac{\delta}{2} e^{i(\pi/2-2\theta)} \end{bmatrix}$$

If the coordinates of the observing system are rotated by 45°, the output light X0-45 is then given by the following vector:

$$X0\text{-}45 = \begin{bmatrix} \cos\frac{\delta}{2} \\ \sin\frac{\delta}{2} e^{i(\pi/2-2\theta)} \end{bmatrix}$$

The axial direction $\eta$ of the elliptical polarization which is then detected, is given by equation (3):

$$\tan 2\eta = \tan \delta \sin 2\theta \quad (3)$$

$\delta$ and $\theta$ may be found from the following relations:

$$\delta = \tan^{-1}\sqrt{\tan^2 2\xi + \tan^2 2\eta}$$

$$\theta = \frac{1}{2}\tan^{-1}\left(-\frac{\tan 2\eta}{\tan 2\xi}\right)$$

The above computation is performed for each picture element of the image sensor, and birefringence information for all parts of the specimen may thus be analyzed in one step.

When the analysis is completed, the retardation is expressed as a light or dark shade on the display terminal 43, or converted to a dot size and printed out. This gives an overall visual representation of the scatter in the birefringence of the specimen.

In the above embodiment, we have described only the case where a two dimensional measurement is made using an image sensor. The invention is not, however, limited to this case, and is also effective to measure the birefringence of part of a specimen using a narrow light beam.

Further, in the above embodiment, measurements were performed in a first step and second step by rotating the second $\frac{1}{4}$ wave plate 32. The same measurements may, however, be made by interchanging two $\frac{1}{4}$ wave plates with different neutral axes.

EMBODIMENT 6

Figure 14:
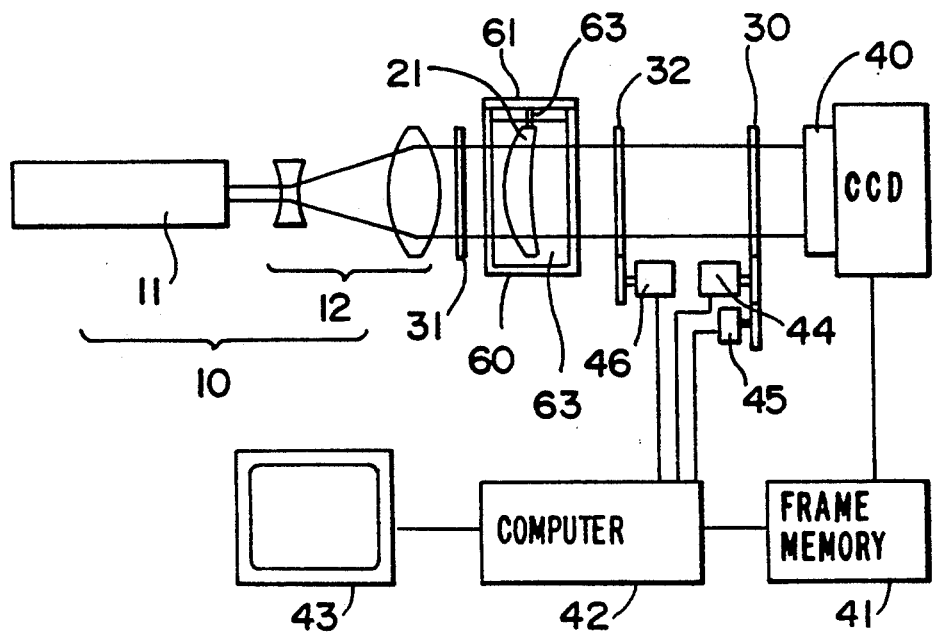
FIG. 14 is a schematic drawing of a sixth embodiment of a birefringence measuring device of the present invention.

FIG. 14 shows a sixth embodiment of the polarization and birefringence measuring device of this invention.

In this embodiment, a test lens 21 is immersed in a matching fluid 63 in a tank 60. The construction of the tank is identical to that of the embodiment of FIG. 11, and other features are the same as those of the embodiment shown in FIG. 13.

In this device, information concerning the distribution of birefringence in the material of the specimen may be obtained without detecting the change in polarization state due to the shape of the lens or other optical elements.

What is claimed is:

1. A polarization and birefringence measuring device, comprising:
   an optical source which causes a wide polarized light beam to impinge on a specimen;
   a photodetecting means for detecting a light beam, said photodetector means having picture elements in two dimensions which detects a light beam containing information about said specimen;
   an analyzer which is situated in front of said photodetecting means and which is rotated to vary an amount of light which is transmitted;
   means for sampling an intensity of each picture element in said photodetecting means when said analyzer is set at no less than three different angles; and
   means for analyzing a polarization state of parts of said specimen corresponding to said intensity of each picture element sampled, said intensity of said light detected by said photodetecting means varying sinusoidally when said analyzer is rotated, wherein said specimen comprises a lens, and an adjusting lens is interposed between said optical source and said specimen that causes said polarized light beam to impinge on said specimen lens such that said polarized light beam emerges in the same way as said polarized light beam would in actual use.

2. A polarization and birefringence measuring device, comprising:
   an optical source which causes a wide polarized light beam to impinge on a specimen;
   a photodetecting means for detecting a light beam, said photodetector means having picture elements in two dimensions which detects a light beam containing information about said specimen;
   an analyzer which is situated in front of said photodetecting means and which is rotated to vary an amount of light which is transmitted;
   means for sampling an intensity of each picture element in said photodetecting means when said analyzer is set at no less than three different angles; and
   means for analyzing a polarization state of parts of said specimen corresponding to said intensity of each picture element sampled, said intensity of said light detected by said photodetecting means varying sinusoidally when said analyzer is rotated, wherein said specimen comprises a lens, and an adjusting lens is interposed between said optical source and said specimen lens that causes said polarized light beam to impinge on said specimen lens such that said polarized light beam is parallel when said polarized light beam emerges.

3. A polarization and birefringence measuring device, comprising:
   an optical source which causes a wide polarized light beam to impinge on a specimen;
   photodetecting means for detecting a light beam, said photodecting means having picture elements in two dimensions which detect a light beam containing information about said specimen;
   an analyzer which is situated in front of said photodetecting means and which is rotated to vary an amount of light which is transmitted;
   a first phase shifter that is interposed between said optical source and said specimen;
   a second phase shifter that is interposed between said specimen and said analyzer, said second phase shifter being free to rotate about an optical axis;
   means for sampling an intensity of each picture element in said photodetecting means, wherein said sampling means samples said intensity at no less than three different angles of said analyzer when said second phase shifter is set at a first predetermined angle and samples said intensity at no less than three different angles of said analyzer when said second phase shifter is set at a second predetermined angle; and
   means for analyzing a polarization state of parts of said specimen corresponding to said intensity of each picture element sampled, said intensity of light detected by said photodetecting means varying sinusoidally when said analyzer is rotated.

4. The device of claim 3, wherein said first and second phase shifters comprise ¼ wave plates.

5. A polarization and birefringence measuring device, comprising:
   an optical source which causes a wide polarized light beam to impinge on a specimen;
   photodetecting means for detecting a light beam, said photodecting means having picture elements in two dimensions which detect a light beam containing information about said specimen;
   an analyzer which is situated in front of said photodetecting means and which is rotated to vary an amount of light which is transmitted;
   a first phase shifter that is interposed between said optical source and said specimen;
   a second phase shifter that is interposed between said specimen and said analyzer, said second phase shifter being free to rotate about an optical axis;
   means for sampling an intensity of each picture element in said photodetecting means, wherein said sampling means samples said intensity at no less than three different angles of said analyzer when said second phase shifter is set at a first predetermined angle and samples said intensity at no less than three different angles of said analyzer when said second phase shifter is set at a second predetermined angle; and
   means for analyzing a polarization state of parts of said specimen corresponding to said intensity of each picture element sampled, said intensity of said light detected by said photodetecting means varying sinusoidally when said analyzer is rotated, said second phase shifter comprising a freely interchangeable part.

6. The device of claim 5, wherein said first and second phase shifters comprise ¼ wave plates.

7. A polarization and birefringence measuring device, comprising:
   an optical source which emits a polarized light beam that impinges on a test lens;
   an adjusting lens that causes said polarized light beam to impinge on said test lens such that it emerges in the same way as it would in actual use;
   photodetecting means for detecting a light beam transmitted by said test lens; and
   an analyzer that is interposed between said test lens and said photodetecting means and which is rotated to vary an amount of transmitted light.

8. A polarization and birefringence measuring device according to claim 7, wherein said photodetecting means has picture elements arranged in two dimensions.

9. A polarization and birefringence measuring device according to claim 8, wherein said device has an imaging lens which forms an image of said test lens on said photodetecting means.

10. A polarization and birefringence measuring device, comprising:
    an optical source which emits a polarized light beam that impinges on a test lens;
    an adjusting lens which causes said polarized light beam to impinge on said test lens such that said polarized light beam is parallel when it emerges;
    photodetecting means for detecting a light beam transmitted by said test lens; and
    an analyzer that is interposed between said test lens and said photodetecting means and which is rotated to vary an amount of transmitted light.

11. A polarization and birefringence measuring device according to claim 10, wherein said photodetecting means has picture elements arranged in two dimensions.

12. A polarization and birefringence measuring device according to claim 10, wherein said device has an imaging lens which forms an image of said test lens on said photodetecting means.

13. A polarization and birefringence measuring device, comprising:

an optical source which causes a wide polarized light beam to impinge on a specimen;

photodetecting means for detecting a light beam, said photodetecting means having picture elements in two dimensions which detect a light beam containing information about said specimen;

an analyzer which is interposed between said specimen and said photodetecting means, and which is rotated to vary an amount of transmitted light;

a first phase shifter that is interposed between said optical source and said specimen;

a second phase shifter that is interposed between said specimen and said analyzer;

means for sampling an intensity of each picture element in said photodetecting means, wherein said sampling means samples said intensity at no less than three different angles of said analyzer when said second phase shifter is set at a first predetermined angle and samples said intensity at no less than three different angles of said analyzer when said second phase shifter is set at a second predetermined angle;

means for analyzing polarization properties of parts of said specimen corresponding to said intensity of each picture element sampled, said intensity of said light detected by said photodetecting means varying sinusoidally when said analyzer is rotated; and means for measuring a birefringence of said specimen by combining results of said analyzing means when said second phase shifter is set at no less than two different angles, said second phase shifter being free to rotate about an optic axis.

14. The device of claim 13, wherein said first and second phase shifters comprise ¼ wave plates.

15. A polarization and birefringence measuring device, comprising:

an optical source which causes a wide polarized light beam to impinge on a specimen;

photodetecting means for detecting a light beam, said photodetecting means having picture elements in two dimensions which detect a light beam containing information about said specimen;

an analyzer which is interposed between said specimen and said photodetecting means, and which is rotated to vary an amount of transmitted light;

a first phase shifter that is interposed between said optical source and said specimen;

a second phase shifter that is interposed between said specimen and said analyzer;

means for sampling an intensity of each picture element in said photodetecting means, wherein said sampling means samples said intensity at no less than three different angles of said analyzer when said second phase shifter is set at a first predetermined angle and samples said intensity at no less than three different angles of said analyzer when said second phase shifter is set at a second predetermined angle;

means for analyzing polarization properties of parts of said specimen corresponding to said intensity of each picture element sampled, said intensity of said light detected by said photodetecting means varying sinusoidally when said analyzer is rotated; and means for measuring a birefringence of said specimen by combining results of said analyzing means when said second phase shifter is set at no less than two different angles, said second phase shifter comprising a freely interchangeable part.

16. The device of claim 15, wherein said first and second phase shifters comprise ¼ wave plates.

* * * * *